United States Patent [19]

Rocher et al.

[11] Patent Number: 5,753,239
[45] Date of Patent: May 19, 1998

[54] BI-AROMATIC COMPOUNDS AND PHARMACEUTICAL AND COSMETIC COMPOSITIONS

[75] Inventors: Jean-Philippe Rocher, Gaillard; Jean-Michel Bernardon, Nice, both of France

[73] Assignee: Centre International de Recherches Dematologiques Galderma (Cird Galderma), Valborne, France

[21] Appl. No.: 471,356

[22] Filed: Jun. 6, 1995

Related U.S. Application Data

[60] Division of Ser. No. 311,790, Sep. 26, 1994, which is a continuation-in-part of Ser. No. 883,866, May 15, 1992, abandoned.

[30] Foreign Application Priority Data

May 15, 1991 [FR] France ................................ 91 05883

[51] Int. Cl.$^6$ ................................ A61K 9/00
[52] U.S. Cl. .............. 424/401; 424/70.1; 424/400; 424/422; 424/427; 546/304; 546/329; 549/68; 549/74; 560/13; 560/35; 562/427; 562/440; 564/162; 564/245; 514/166; 514/231.2; 514/231.5; 514/231.8; 514/252; 514/255; 514/315; 514/316; 514/317; 514/326; 514/327; 514/331; 514/422; 514/426; 514/438; 514/444; 514/448; 514/461; 514/471; 514/508; 514/514; 514/532; 514/543; 514/557; 514/576; 514/637; 514/726; 514/731; 514/741; 514/562; 514/564; 514/567

[58] Field of Search ................................ 546/304, 329; 549/68, 74, 480, 491, 492; 560/13, 35; 562/427, 440; 564/167, 164, 245; 514/166, 231.2, 231.5, 231.8, 252, 255, 315–317, 326, 327, 339, 331, 422–424, 426–428, 438, 444, 445, 448, 461, 471–473, 508, 514, 532, 543, 544, 557–562, 564, 567–570, 576, 577, 637, 641, 726, 731–741; 424/400, 401, 70.1, 422, 427

[56] References Cited

U.S. PATENT DOCUMENTS 3,669,974  6/1972  Elpern et al. ................................ 546/231
4,264,505  4/1981  Shroff et al. ................................ 260/326.5

FOREIGN PATENT DOCUMENTS 0232199  8/1987  European Pat. Off. .
465343  1/1992  European Pat. Off. .

OTHER PUBLICATIONS

Chemical Abstracts, vol. 92, No. 9, Mar. 1980, Abstract No. 76036M, Albu, "Cumylphenol Derivatives, III. Synthesis and Electronic Spectra Ofsome Cumylphenol–Derived Arylazomethines".

Chemical Abstracts, vol. 77, No. 17, Oct. 1972, Abstract No. 113925, Bruk et al, "Screened Phenols. VI. Azomethines, Derivatives of 3,5–Di–Tert–Butyl–4–Hydroxybenzaldehyde".

Chemical Abstracts, vol. 111, No. 7, Aug. 1989, Abstract No. 56768J, Ivakhnenko et al, "Synthesis of Sterically Hindered Diarylamidine Phenols and Properties of Radicals Formed From Them".

French Search Report of FR 91 05883.

Vila et al, Synth. React. Inorg. Met. –Org. Chem. 1988 18(1)47–67 cited in Chem. Abstract vol. 110:213030M vol. 110, 1989.

Ivakhnenko et al, Zh. Org. Khim. 1989 (25(2)357–367 cited in Chem. Abstract vol. 111, 1989, p. 674 111:56768.

Makovec et al, J.Med. Chem. 35(20) 3633–40 1992 cited in Chem. Abstract vol. 117(17) 170914C.

Kato et al, WO 9111994 Aug. 22, 1991, cited in Chem. Abstract 116(12):128356b.

Bruk, CA vol. 77, 1972 113922k p. 409 Screened phenols VI Azomethines.

Manda, CA vol. 82, 1975 42507M p. 367 synthesis & oxidation of 4–(N–arylmethylidenea ino–2,6–di–tert butylphenols.

*Primary Examiner*—Neil S. Levy
*Attorney, Agent, or Firm*—Nixon & Vanderhye, P.C.

[57] ABSTRACT

Bi-aromatic compounds are provided along with methods for their preparation and use.

16 Claims, No Drawings

BI-AROMATIC COMPOUNDS AND PHARMACEUTICAL AND COSMETIC COMPOSITIONS

This is a division of application Ser. No. 08/311,790, filed Sep. 26, 1994, which is a continuation-in-part of application Ser. No. 07/883,866, filed May 15, 1992, now abandoned.

The present invention relates to new aromatic compounds, to their preparation and to their use in human and veterinary medicine and in cosmetic compositions.

These new compounds are usefully employed in the topical and systemic treatment of dermatologic ailments linked to a keratinization disorder (differentiation-proliferation) and dermatologic disorders, or others having an inflammatory and/or immuno-allergic component and in conjunctive tissue degenerative diseases. They also exhibit an anti-tumoral activity. Moreover, these compounds can be employed in the treatment of atopy be it cutaneous or respiratory, and in the treatment of rheumatoid psoriasis.

The compounds are also useful in the ophthalmological field and in particular in the treatment of corneopathies.

The compounds according to the invention can be represented by the following general formula

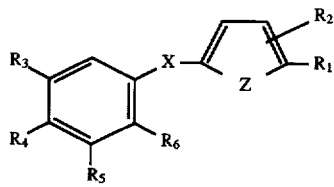  (I)

wherein $R_1$ represents hydrogen, OH, —$CH_3$, —$CH_2OH$, —$COR_7$, —$CH(OH)CH_3$, —$CH_2OCOR_8$, —$SO_2R_9$, —$SOR_9$ or $SR_9$, $R_7$ represents hydrogen, OH, —$OR_{10}$,

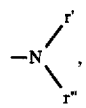

lower alkyl, monohydroxyalkyl, polyhydroxyalkyl or the residue of a sugar, $R_8$ represents linear or branched alkyl having 1–20 carbon atoms, alkenyl having 2 to 20 carbon atoms or the residue of a sugar, $R_9$ represents OH, lower alkyl or

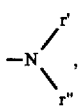

$R_{10}$ represents alkyl having 1–20 carbon atoms or alkenyl having 2–20 carbon atoms, r' and r", each independently, represent hydrogen, lower alkyl, aryl, aralkyl, the residue of an amino acid, the residue of a sugar, the residue of an aminated sugar or a heterocycle, or r' and r" taken together form a heterocycle, $R_2$ and $R_6$ represent hydrogen, OH, lower alkyl, alkoxy having 1–6 carbon atoms, fluorine, chlorine or $CF_3$, $R_3$ and $R_5$ represent α,α'-disubstituted alkyl having 4–12 carbon atoms or mono or polycyclic cycloalkyl having 5 to 12 carbon atoms whose linking carbon is trisubstituted, $R_5$ is hydrogen, $R_4$ represents hydrogen, OH, alkoxy having 1–6 carbon atoms or α,α'-disubstituted alkyl having 4–12 carbon atoms, $R_3$ and $R_4$ or $R_4$ and $R_5$ taken together form, with the adjacent benzene ring, a ring having 5 or 6 carbon atoms substituted by 2 to 6 methyl groups, Z represents oxygen or sulfur, the divalent radical —CH=$CR_{11}$— or the divalent radical —N=$CR_{12}$—, $R_{11}$ represents hydrogen, OH or lower alkyl, $R_{12}$ represents hydrogen or lower alkyl, X is selected from the group consisting of —$CR_{13}$=N—,  (i)

—N=$CR_{13}$—,  (ii)

—C—$NR_{14}$, and  (iii)
 ‖
 N—$R_{15}$

—$NR_{14}$—C—  ,  (iv)
       ‖
       N—$R_{15}$ $R_{13}$ represents $R_{16}$, $OR_{16}$, —$SR_{16}$ or

$R_{16}$ and $R_{17}$ represent hydrogen, lower alkyl, fluoro lower alkyl, alkenyl having 2–6 carbon atoms, alkynyl having 2–6 carbon atoms, aryl or aralkyl, $R_{14}$ represents lower alkyl, $R_{15}$ represents lower alkyl or fluoro lower alkyl, with the exclusion of compounds of Formula (I) in which $R_3$ and $R_5$ are identical when X represents —$CR_{13}$=N—, wherein $R_{13}$ represents hydrogen.

The present invention also relates to the salts of these compounds formed from bases as well as from acids and the optical isomers of the said compounds of Formula (I).

When the compounds according to the invention are provided in salt form, by the addition of a base, it is a question of salts of an alkali or alkaline earth metal or even of zinc or an organic amine.

When the compounds are provided in salt form by the addition of an acid, it is a question of pharmaceutically or cosmetically acceptable salts obtained by the addition of a mineral or organic acid, in particular, hydrochloric acid, sulfuric acid, acetic acid, citric acid, fumaric acid, hemisuccinic acid, maleic acid and mandelic acid.

By lower alkyl is meant alkyl having from 1 to 6 carbon atoms and preferably methyl, ethyl, isopropyl, butyl and tert.butyl.

By alkoxy having 1 to 6 carbon atoms is meant, preferably, methoxy, ethoxy, isopropoxy or butoxy.

By α,α'-disubstituted alkyl having 4–12 carbon atoms is meant, principally, tert. butyl, 1,1-dimethyl propyl, 1-methyl-1-ethyl propyl, 1-methyl-1-ethyl hexyl or 1,1-dimethyl decyl.

By mono or polycyclic cycloalkyl having 5–12 carbon atoms whose linking carbon is trisubstituted is meant 1-methyl cyclohexyl or 1-adamantyl.

By monohydroxyalkyl is meant a radical having 1–6 carbon atoms, principally, 2-hydroxyethyl, 2-hydroxypropyl or 3-hydroxypropyl.

By polyhydroxyalkyl is meant a radical containing 2–6 carbon atoms and 2–5 hydroxyl groups such as 2,3-dihydroxypropyl, 2,3,4-trihydroxybutyl, 2,3,4,5-tetrahydroxypentyl or the residue of pentaerythritol.

By aryl is meant phenyl, optionally substituted by at least one halogen, hydroxyl or nitro function.

By aralkyl is meant benzyl or phenylethyl optionally substituted by at least one halogen, hydroxyl or nitro function.

By alkenyl having 2–6 carbon atoms is meant principally vinyl, propenyl, 2-methylpropenyl or buten-2-yl.

By alkynyl having 2–6 carbon atoms is meant principally propargyl.

By fluoro lower alkyl is meant a radical having 1–6 carbon atoms and 3–7 fluorine atoms, such as —$CF_3$ and $C_2F_5$.

When $R_8$ or $R_{10}$ represent alkyl having 1–20 carbon atoms or alkenyl having 2 to 20 carbon atoms, they are linear or branched radicals optionally substituted by one or more hydroxyl groups or one or more fluorine atoms.

By amino acid residue is meant a residue derived, for example, from one of the 20 amino acids having L or D configuration (or their racemic mixture) constitutive of mammalian proteins.

By sugar residue is meant a residue derived, for example, from glucose, galactose or mannose.

By aminated sugar residue is meant a residue derived, for example, from glucosamine, galactosamine or mannosamine.

By heterocycle is meant, preferably, piperidino, morpholino, pyrrolidino or piperazino, optionally substituted in position 4 by a $C_1$–$C_6$ alkyl or a mono or polyhydroxyalkyl such as defined above.

Principal among the compounds of Formula (I), given above, are the following:

4-(α-methylamino-5,6,7,8-tetrahydro-5,5,8,8-tetramethyl-2-naphthylmethylideneamino)benzoic acid, 4-(α-amino-5,6,7,8-tetrahydro-5,5,8,8-tetramethyl-2-naphthylmethylideneamino)benzoic acid, 4-[5-(1-adamantyl)-2-hydroxy-4-methoxybenzylideneamino]benzoic acid, 4-[α-amino-3-(1-adamantyl)-4-methoxybenzylideneamino]benzoic acid, the hydrochloride of 4-[α-methylamino-3-(1-adamantyl)-4-methoxybenzylideneamino]benzoic acid, 4-[α-methylthio-3-(1-adamantyl)-4-methoxybenzylideneamino]benzoic acid, 4-[α-methoxy-3-(1-adamantyl)-4-methoxybenzylideneamino]benzoic acid, methyl 4-[3-(1-adamantyl)-4-methoxybenzylideneamino]benzoate, 4-[3-(1-adamantyl)-4-methoxybenzylideneamino]benzoic acid, 4-(α-amino-3-tert.butyl-4-methoxybenzylideneamino)benzoic acid, methyl 4-(α-amino-5,6,7,8-tetrahydro-5,5,8,8-tetramethyl-2-naphthylmethylideneamino)benzoate, 4-(α-amino-5,6,7,8-tetrahydro-5,5,8,8-tetramethyl-2-naphthylmethylideneamino)benzyl alcohol, 4-(α-amino-5,6,7,8-tetrahydro-5,5,8,8-tetramethyl-2-naphthylmethylideneamino)toluene, 4-(α-amino-5,6,7,8-tetrahydro-5,5,8,8-tetramethyl-2-naphthylmethylideneamino)benzamide, 2-hydroxy-4-(α-amino-5,6,7,8-tetrahydro-5,5,8,8-tetramethyl-2-naphthylmethylideneamino)benzoic acid, allyl 4-(α-chloro-5,6,7,8-tetrahydro-5,5,8,8-tetramethyl-2-naphthylmethylideneamino)benzoate, 4-(α-anilino-5,6,7,8-tetrahydro-5,5,8,8-tetramethyl-2-naphthylmethylideneamino)benzoic acid, the hydrochloride of 4-(α-anilino-5,6,7,8-tetrahydro-5,5,8,8-tetramethyl-2-naphthylmethylideneamino)benzoic acid, 4-(α-benzylamino-5,6,7,8-tetrahydro-5,5,8,8-tetramethyl-2-naphthylmethylideneamino)benzoic acid, 4-(α-dimethylamino-5,6,7,8-tetrahydro-5,5,8,8-tetramethyl-2-naphthylmethylideneamino)benzoic acid, 4-[$N^2$-(5,6,7,8-tetrahydro-5,5,8,8-tetramethyl-2-naphthyl)amidino]benzoic acid, 4-[$N^1$-phenyl-$N^2$-(5,6,7,8-tetrahydro-5,5,8,8-tetramethyl-2-naphthyl)amidino]benzoic acid, the hydrochloride of 4-(α-amino-5,6,7,8-tetrahydro-5,5,8,8-tetramethyl-2-naphthylmethylideneamino)phenol, 4-(α-methylamino-N-methyl-5,6,7,8-tetrahydro-5,5,8,8-tetramethyl-2-naphthylmethylamino)benzoic acid, and 4-[α-(2,2,2-trifluoroethylamino)-5,6,7,8-tetrahydro-5,5,8,8-tetramethyl-2-naphthylmethylamino)benzoic acid.

The present invention also relates to, as intermediate compounds, those of the formula

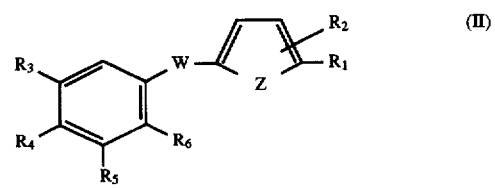

(II)

wherein

W represents a radical selected from the group consisting of:

(i)

(ii)

(iii)

(iv)

Z and $R_2$ to $R_6$ have the same meanings given above for Formula (I).

$R_1$ has the same meaning given above for Formula (I) when W is either the radical (i) or the radical (ii), or $R_1$ represents the radical —$COOCH_2$—$CH$=$CH_2$ when W is either the radical (iii) or the radical (iv).

The present invention also relates to the process for preparing the compounds of Formula (I).

When X represents an imine link with X=(i) the compounds are obtained by the reaction of a benzaldehyde substituted with a para-amino allyl benzoate, optionally substituted, in an anhydrous solvent such as methylene chloride in the presence of dehydrating agent, for example, basic alumina.

When X represents an imine link with X=(ii) the compounds are obtained by the reaction of a substituted aniline on an aromatic aldehyde substituted by an acid function which is protected in the form of an allylic ester under the same preceding conditions.

When X represents an imidate, thioimidate or amidine link with X=(i), the compounds according to the invention are prepared in accordance with the following reaction scheme:

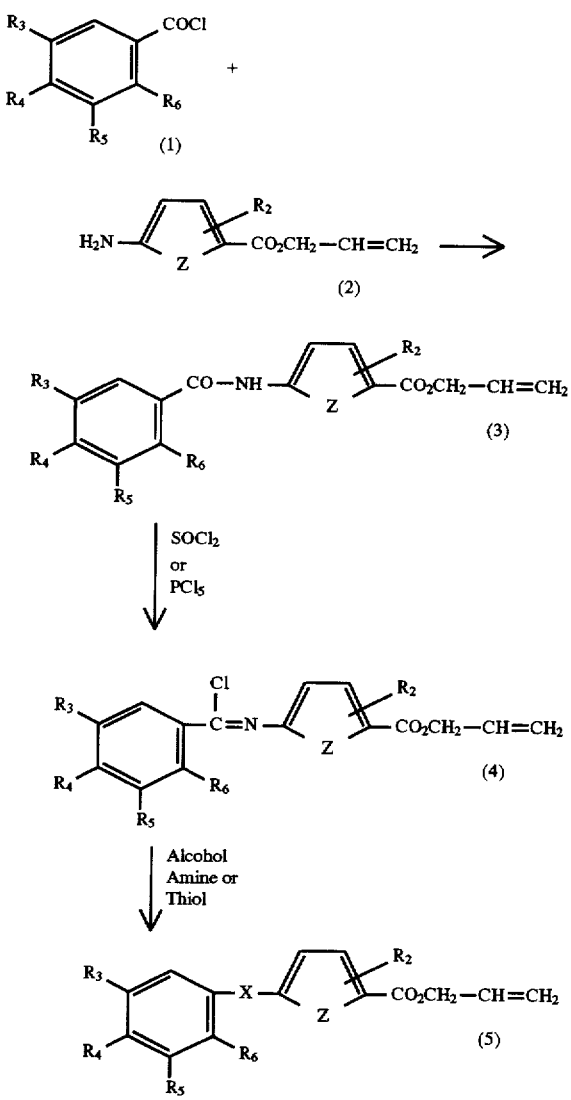

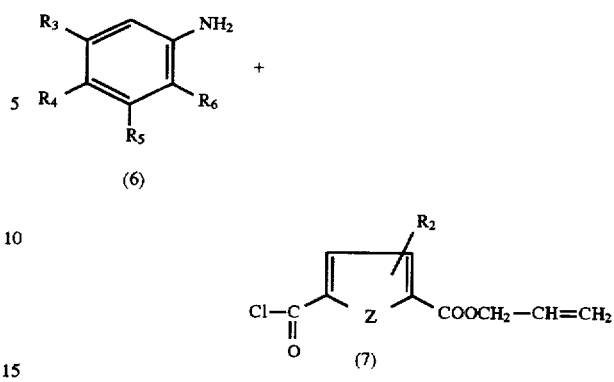

The first step consists in reacting in an anhydrous medium, in an organic solvent such as tetrahydrofuran or methylene chloride containing a tertiary amine (pyridine or triethylamine) an activated form of a substituted benzoic acid, for example, an acid chloride (1) or a mixed anhydride on a para-amino allyl benzoate optionally substituted (2). The reaction is conducted at ambient temperature and with stirring.

The amide (3) thus obtained is converted into an iminochloride (4) by the action of thionyl chloride, phosphorus pentachloride or phosgene.

By the reaction of compound (4) with an amine, an alcohol or a thiol in the presence of a tertiary amine and an alkaline hydride in an organic solvent such as tetrahydrofuran or methylene chloride, the compound of formula (5) is obtained.

When X represents an imidate, thioimidate or amidine link with X=(ii) the preparation is carried out in the same manner as above by starting with the following compounds (6) and (7):

The passage of the ester to the free acid can be effected in the 4 cases above by means of a catalyst, such as certain transition metal complexes, for example, tetrakis triphenyl 2phosphine palladium (0) in the presence of a secondary amine or the sodium salt of diethyl malonate or in an alkaline medium, preferably in the presence of a methanolic soda solution.

When X represents an amidine link corresponding to formulas (iii) and (iv) the synthesis is carried out in accordance with the conventional Pinner process by condensing a substituted aniline with an aromatic nitrile.

The present invention also relates to, as a medicine, the compounds of Formula (I) as defined above.

The compounds according to the invention exhibit good stability to light and oxygen.

These compounds exhibit an activity in the differentiation test of embryonic teratocarcinoma cells of mice (F9) (Cancer Research 43 p. 5268. 1983) and/or in the inhibition test of ornithine decarboxylase after induction by TPA in mice (Cancer Research 38, p. 793–801, 1978). These tests show the activity of the compounds, respectively, in the areas of differentiation and proliferation.

The compounds according to the invention are indeed particularly appropriate in the following treatment areas:

(1) to treat dermatologic ailments linked to a keratinization disorder causing differentiation and proliferation and principally for treating acne vulgaris, comedones, polymorphs, nodulokystic acne, conglobata, senile acne, secondary acne such as solar, medicinal or professional acne;

(2) to treat other types of keratinization disorders, principally ichtyoses, ichthyosiform conditions, Darrier malady, leucoplasiforms, cutaneous or mucous lichen;

(3) to treat dermatologic ailments linked to a keratinization disorder having an inflammatory and/or immunoallergic component and, principally, all forms of psoriasis be they cutaneous, mucous or ungual, and even psoriatic rheumatism, or again cutaneous atopy, such as eczema, or respiratory atopy or gingival hypertrophy; the compounds can also be employed in certain inflammatory conditions not exhibiting any keratinization disorder;

(4) to treat all dermic or epidermic proliferations that are benign or malignant, that are of viral origin such as common warts, planar warts and epidermodysplasie verruciform, florid oral papillomatosis, the proliferation being able also to be induced by ultraviolet radiation, principally in the case of baso epithelioma and cellular spino;

(5) to treat other dermatologic disorders such as blistery dermatoses and collagen maladies;

(6) to treat certain ophthalmologic disorders, and principally, corneopathies;

(7) to restore or combat against skin aging be it chronologic or photoinduced or to reduce pigmentation and actinic keratosis;

(8) to prevent or heal the scars of epidermic and/or dermic atrophy induced by local or systemic corticosteroids, or any other form of cutaneous atrophy;

(9) to prevent or restore cicatrization disorders or vergetures;

(10) to combat against disorders of the sebaceous function, such as hyper seborrhea of acne or simple seborrhea;

(11) in the treatment of cancerous or precancerous situations in particular at the cutaneous level; and

(12) in the treatment of inflammatory conditions, such as arthritis.

The present invention also related to medicinal compositions containing at least one compound of Formula (I) such as defined above, or one of its salts.

The present invention relates then to a new medicinal composition intended principally for the treatment of the abovementioned conditions comprising, in a pharmaceutically acceptable support, at least one compound of Formula (I) and/or one of its salts.

The compounds according to the invention are generally administered at a daily dosage of about 0.01 mg/kg to 100 mg/kg of body weight in 1 or 3 doses.

The administration can be effected enterally, parenterally, topically or ocularly. When administered enterally, the medicine can be provided in the form of tablets, gelules, dragees, syrups, suspensions, solutions, powders, granules and emulsions. When administered parenterally, the compositions can be provided in the form of solutions or suspensions for perfusion or injection.

When administered topically, the pharmaceutical compositions based on the compounds in accordance with the invention are intended for the treatment of the skin and mucous membranes and are provided in the form of an ointment, cream, milk, pomade, powder, impregnated pads, solutions, gels, sprays, lotions or suspensions. They can also be provided in the form of microspheres or nanospheres or ionic or nonionic or polymeric lipidic vesicles or polymeric patches or hydrogels which permit controlled release.

These topically applied compositions can be provided either under anhydrous form or under aqueous form in accordance with clinical indications.

When administered ocularly, they are principally eyewashes.

These compositions contain at least one compound of formula (I) such as defined above or one of its salts, in an amount preferably ranging from 0.001 to 5 percent by weight relative to the total weight of the composition.

The compounds of Formula (I), according to the invention, also find use in the cosmetic field, in particular, in body and hair hygiene, and principally for the treatment of skin having acne tendencies, for hair growth, to combat hair loss, to combat against the oily appearance of the skin or hair, in the protection against the harmful effects of the sun or in the treatment of physiologically dry skin.

The present invention thus also envisions a cosmetic composition containing in a cosmetically acceptable support at least one compound of Formula (I) or one of its salts, this composition being provided principally in the form of a cream, a milk, a lotion, a gel, microspheres or nanospheres or lipidic or polymeric vesicles, a soap or a shampoo composition.

The concentration of the compound of Formula (I) in the cosmetic compositions ranges, principally, from 0.001 to 3 percent by weight based on the total weight of the composition.

The medicinal and cosmetic compositions according to the invention can also contain inert or even pharmacodynamic or cosmetically active additives or combinations thereof and principally: wetting agents; depigmenting agents such as hydroquinone, azelaic acid, caffeic acid, kojic acid; emollient agents; hydrating agents such as glycerol, PEG 400, thiamorpholinone and its derivatives or urea; antiseborrhea or anti-acne agents, such as S-carboxymethylcysteine, S-benzylcysteamine, their salts and their derivatives, tioxolone or benzoyl peroxide; antibiotics such as erythromycin and its esters, neomycin, clindamycin and its esters and tetracyclines; antifungus agents such as ketoconazole or 4,5-polymethylene-3-isothiazolinones; agents promoting hair growth such as "Minoxidil" (2,4-diamino-6-piperidino-pyrimidine-3-oxide) and its derivatives, Diazoxide(7-chloro-3-methyl-1,2,4-benzothiadiazine-1,1-dioxide) and Phenytoin(5,5-diphenyl-imidazolidine-2,4-dione); steroidal and non-steroidal anti-inflammatory agents; carotenoids and principally, β-carotene; anti-psoriatic agents such as anthralin and its derivatives and 5,8,11,14-eicosatetraynoic and 5,8,11-eicosatriynoic acids, their esters and their amides; or anti-irritant agents such as derivatives of α-hydroxy acids and more particularly the derivatives of mandelic acid.

The compositions according to the invention can also contain flavor improving agents, preservatives such as esters of parahydroxybenzoic acid, stabilizers, humidity regulating agents, pH regulating agents, osmotic pressure modifying agents, emulsifying agents, UV-A and UV-B filters, and antioxidants such as α-tocopherol, butylhydroxyanisole and butylhydroxytoluene.

The following non-limiting examples illustrate the preparation of the active compounds of Formula (I) according to the invention as well as examples of compositions containing these compounds.

EXAMPLE 1

4-(α-methylamino-5,6,7,8-tetrahydro-5,5,8,8-tetramethyl-2-naphthylmethylideneamino)benzoic acid (a) allyl 4-(5,6,7,8-tetrahydro-5,5,8,8-tetramethyl-2-naphthylcarboxamido)benzoate In a round bottom flask, there are introduced 2.8 g (16 mmoles) of allyl 4-aminobenzoate, 2.5 ml (16 mmoles) of triethylamine and 50 ml of THF. A solution of 4.3 g (16 mmoles) of 5,6,7,8-tetrahydro-5,5,8,8-tetramethyl-2-naphthoyl chloride dissolved in 50 ml of THF is slowly added and the mixture is stirred at ambient temperature for 2 hours. The reaction medium is poured into water and extracted with ethyl ether. The organic phase is decanted, dried on magnesium sulfate and evaporated. The resulting residue is purified by chromatography on a silica column, eluted with a 60/40 mixture of dichloromethane and hexane. After evaporation of the solvents 5.7 g of the expected ester having a melting point of 148°–149° C. are obtained.

(b) allyl 4-(α-chloro-5,6,7,8-tetrahydro-5,5,8,8-tetramethyl-2-naphthylmethylideneamino)benzoate In a round bottom flask, there are introduced 3.9 g (10 mmoles) of the ester obtained in Example 1 (a) and 50 ml of thionyl chloride. The mixture is heated at reflux for 24 hours and is then evaporated to dryness. 4.4 g (100%) of the expected crude product is recovered and is employed, as such, for the following synthesis.

(c) allyl 4-(α-methylamino-5,6,7,8-tetrahydro-5,5,8, 8-tetramethyl-2-naphthylmethylideneamino) benzoate In a round bottom flask, there are introduced 2.2 g (0.05 mole) of the compound obtained above in 1(b) and while cooling to 0° C., 50 ml of methylamine (40% in water) are slowly added. The mixture is stirred at ambient temperature for 1 hour. The reaction medium is poured into water and extracted with ethyl ether. The organic phase is decanted, dried on magnesium sulfate and evaporated. The resulting residue is purified by chromatography on a silica column, eluted with a 90/10 mixture of dichloromethane and ethyl ether. After evaporation of the solvents, 1.6 g (79%) of a slightly yellow oil is obtained.

(d) 4-(α-methylamino-5,6,7,8-tetrahydro-5,5,8,8-tetramethyl-2-naphthylmethylideneamino)benzoic acid In a round bottom flask, there are introduced 1.4 g (3.4 mmoles) of the allylic ester obtained above in 1(c) and 50 ml of THF. Under nitrogen 400 mg (0.35 mmole) of tetrakis (triphenylphosphine)palladium (0) are introduced and 3 ml (34 mmoles) of morpholine are slowly added. The mixture is stirred at ambient temperature for 4 hours and the reaction medium is evaporated to dryness. The resulting residue is taken up in water and acidified to pH=5 with 1N hydrochloric acid. The solid is filtered and dried on phosphorus pentoxide. The solid is purified by chromatography on a silica column, by eluting with an 80/20 mixture of dichloromethane and methanol. 850 mg (68%) of the expected acid having a melting point of 164°–167° C. (with decomposition) are obtained.

EXAMPLE 2

4-(α-amino-5,6,7,8-tetrahydro-5,5,8,8-tetramethyl-2-naphthylmethylideneamino)benzoic acid (a) allyl 4-(α-amino-5,6,7,8-tetrahydro-5,5,8,8-tetramethyl-2-naphthylmethylideneamino)benzoate In a manner analogous to Example 1(c) by reacting 22 g (0.05 mole) of the compound obtained in Example 1(b) with 50 ml of ammonia (33%) 1.8 g (92%) of the expected allylic ester are obtained in the form of a yellow oil.

(b 4-(α-amino-5,6,7,8-tetrahydro-5,5,8,8-tetramethyl-2-naphthylmethylideneamino)benzoic acid In a manner analogous to Example 1(d) starting with 1.6 g (4.1 mmoles) of allyl α-amino-4-(5,6,7,8-tetrahydro-5,5, 8,8-tetramethyl-2-naphthylmethylideneamino)benzoate 710 mg (51%) of the expected acid having a melting point of 192°–195° C. (with decomposition) are obtained.

EXAMPLE 3

4-[5-(1-adamantyl)-2-hydroxy-4-methoxybenzylideneamino]benzoic acid (a) 2-hydroxy-4-methoxybenzaldehyde In a round bottom flask, there are introduced 6 g (0.2 mole) of sodium hydride (80% in oil) and 50 ml of DMF. A solution of 27.6 g (0.2 mole) of 2,4-dihydroxybenzaldehyde in 100 ml of DMF is slowly added and the mixture is stirred until the cessation of gaseous emission. There are then slowly added 12.5 ml (0.2 mole) of methyliodide and the mixture is stirred at ambient temperature for 12 hours. The reaction medium is poured into water and extracted with ethyl ether. The organic phase is decanted, dried on magnesium sulfate and evaporated. The resulting residue is purified by chromatography on a silica column by eluting with a 70/30 mixture of dichloromethane and hexane. After evaporation of the solvents, 20.3 g (68%) of the expected product whose melting point is 38°–40° C. are recovered.

(b) 5-(1-adamantyl)-2-hydroxy-4-methoxybenzaldehyde

In a round bottom flask, there are introduced 10.4 g (68 mmoles) of the aldehyde obtained in Example 3(a), 10 g (68 mmoles) of 1-adamantanol and 300 ml of dichloromethane. 3.6 ml of sulfuric acid are slowly added and the mixture is stirred at ambient temperature for 24 hours. The reaction medium is poured into water and extracted with dichloromethane. The organic phase is decanted, washed with water, dried on magnesium sulfate and evaporated. The residue is pulverized in ethanol and filtered. The resulting solid is dried under a vacuum. 14.8 g (76%) of the expected product whose melting point is 191°–193° C. are recovered.

(c) 4-[5-(1-adamantyl)-2-hydroxy-4-methoxybenzylideneamino]benzoic acid

In a round bottom flask, there are introduced 2.86 g (0.01 mole) of the aldehyde obtained above in (b), 1.37 g (0.01 mole) of 4-aminobenzoic acid and 500 ml of ethanol. 540 mg (0.01 mole) of sodium methylate are added and the mixture is heated at reflux and the ethanol is distilled off. The remainder is taken up in water and the pH is adjusted to 5 with citric acid. The resulting solid is filtered, washed with water and dried on phosphorus pentoxide. The solid is ground in 50 ml of ethyl ether and after filtration, 2.9 g (72%) of the expected acid whose melting point is 333°–335° C. are recovered.

EXAMPLE 4

4-[α-amino-3-(1-adamantyl)-4-methoxybenzylideneamino]benzoic acid (a) allyl 4-[3-(1-adamantyl)-4-methoxybenzamido] benzoate In a manner analogous to Example 1(a) starting with 12.6 g (71 mmoles) of allyl 4-aminobenzoate and 21.6 g (71 mmoles) of 3-(1-adamantyl)-4-methoxy benzoyl chloride, 32 g of the expected amide whose melting point is 191°–192° C. are isolated.

(b) allyl 4-[α-chloro-3-(1-adamantyl)-4-methoxyphenylmethylimino]benzoate

Starting with 8.9 g (19.2 mmoles) of the derivative obtained above in (a), a synthesis is carried out following the procedures of Example 1(b). The resulting crude product is washed with ether and 6.5 g (73%) of allyl 4-[α-chloro-3-(1-adamantyl)-4-methoxyphenylmethylimino]benzoate whose melting point is 108°–110° C. are obtained.

(c) allyl 4-[α-amino-3-(1-adamantyl)-4-methoxybenzylideneamino]benzoate

In a manner analogous to Example 1(c), by reacting 5 g (107 mmoles) of the compound obtained above in (b) with 10 ml of ammonia (33%) and after chromatography of the crude product on a silica column eluted with a 40/60 mixture of ethylacetate and petroleum ether, 2.4 g (51%) of the expected product whose melting point is 173°–174° C. are obtained.

(d) 4-[α-amino-3-(1-adamantyl)-4-methoxybenzylideneamino]benzoic acid

In a manner analogous to Example 1(d) starting with 2 g (4.5 mmoles) of allyl 4-[α-amino-3-(1-adamantyl)-4-methoxybenzylideneamino]benzoate, 950 mg (52%) of the expected acid whose melting point is 263°–265° C. are obtained.

EXAMPLE 5

The hydrochloride of 4-(α-methylamino-3-(1-adamantyl)-4-methoxybenzylideneamino]benzoic acid (a) allyl 4-[α-methylamino-3-(1-adamantyl)-4-methoxybenzylideneamino]benzoate In a manner analogous to Example 1(c), by reacting 3.8 g (7.5 mmoles) of the compound prepared in Example 4(b) with 10 ml of methylamine (40% in water), and after chromatography on a silica column eluted with a 40/60 mixture of ethylacetate and petroleum ether, 2.3 g (67%) of the expected product whose melting point is 77°–79° C. are obtained.

(b) Hydrochloride of 4-[α-methylamino-3-(1-adamantyl)-4-methoxybenzylideneamino]benzoic acid In a round bottom flask, there are introduced 2 g (4.4 mmoles) of the allylic ester prepared previously and 43 ml of THF. There are then added, under nitrogen, 437 mg (0.44 mmoles) of tetrakis(triphenylphosphine)palladium (O), 8.8 mmoles of base prepared starting with 1.4 g (8.8 mmoles) of diethyl malonate and 262 mg (8.8 mmoles) of sodium hydride (80% in oil) in 30 ml of THF are slowly added. After stirring the mixture at ambient temperature for 2 hours, the medium is acidified with 20 ml of 1N hydrochloric acid. The recovered precipitate is washed with ether, then recrystallized in ethanol. 1.63 g (81%) of the hydrochloride of 4-[α-methylamino-3-(1-adamantyl)-4-methoxybenzylideneamino]benzoic acid whose melting point is 205°–207° C. are obtained.

EXAMPLE 6

4-[α-methylthio-3-(1-adamantyl)-4-methoxybenzylideneamino]benzoic acid (a) allyl 4-[α-methylthio-3-(1-adamantyl)-4-methoxybenzylideneamino]benzoate In a round bottom flask, 700 mg (10 mmoles) of sodium thiomethylate are suspended in 25 ml of dimethoxymethane. At ambient temperature and under a nitrogen stream, there are slowly introduced 3.5 g (7.6 mmoles) of allyl 4-[α-chloro-3-(1-adamantyl)-4-methoxybenzylideneamino]benzoate obtained in Example 4(b) and dissolved in 50 ml of DME. After 3 hours of reaction, the mixture is poured into water and extracted with ethyl ether. The organic phase is dried on sodium sulfate, then evaporated under a vacuum; the resulting crude product is chromatographed on a silica column eluted with a 20/80 mixture of ethyl ether and hexane. After evaporation of the solvents 2.6 g (73%) of the expected product whose melting point is 50°–53° C. are obtained.

(b) 4-[α-methylthio-3-(1-adamantyl)-4-methoxybenzylideneamino]benzoic acid

In a manner analogous to Example 5(b) starting with 1.5 g (3.2 mmoles) of the allylic ester obtained above in (a) 1.05 g (77%) of 4-[α-methylthio-3-(1-adamantyl)-4-methoxybenzylideneamino]benzoic acid whose melting point is 235°–237° C. are obtained.

EXAMPLE 7

4-[α-methoxy-3-(1-adamantyl)-4-methoxybenzylideneamino]benzoic acid (a) allyl 4-[α-methoxy-3-(1-adamantyl)-4-methoxybenzylideneamino]benzoate In a three-necked flask, there are introduced, under an inert atmosphere, 30 ml of dichloromethane, 1.43 ml (10 mmoles) of triethylamine and 324 μl (8 mmoles) of methanol. The mixture is heated to 50° C., then 3.7 g (8 mmoles) of the iminochloride obtained in Example 4(b) and dissolved in 35 ml of dichloromethane are slowly added. At the end of the addition, one equivalent of methanol, or 324 μm is added. After 4 hours of reaction, the reaction mixture is poured into water, then extracted with dichloromethane. The organic phase is decanted, dried on magnesium sulfate and evaporated to dryness. The resulting liquid residue is chromatographed on a silica column eluted with the aid of a 10/90 mixture of ethyl ether and hexane. After evaporation of the solvents, 1.7 g (46%) of the expected product whose melting point is 85°–87° C are recovered.

(b) 4-[α-methoxy-3-(1-adamantyl)-4-methoxybenzylideneamino]benzoic acid

In a manner analogous to Example 5(b) starting with 1.08 g (2.6 mmoles) of the allylic ester obtained above in (a), 720 mg (67%) of 4-[α-methoxy-3-(1-adamantyl)-4-methoxybenzylideneamino]benzoic acid whose melting point is 224°–225° C. are obtained

EXAMPLE 8

Methyl 4-[3-(1-adamantyl)-4-methoxybenzylideneamino]benzoate 3 g of basic alumina and 1.94 g (12.9 mmoles) of methyl 4-aminobenzoate are mixed in a mortar, then introduced into a round bottom flask. 3 g (11.1 mmoles) of 3-(1-adamantyl)-4-methoxybenzaldehyde in 50 ml of anhydrous dichloromethane are added with stirring. After heating at reflux for 24 hours, the reaction medium is extracted with dichloromethane and evaporated to dryness. The crude product is recrystallized in a mixture of ethyl acetate and acetone. After filtration, 3.4 g (75%) of the expected product whose melting point is 180°–182° C. are obtained.

EXAMPLE 9

4-[3-(1-adamantyl)-4-methoxybenzylideneamino]benzoic acid (a) allyl 4-[3-(1-adamantyl)-4-methoxybenzylideneamino]benzoate Starting with 3.4 g (12.6 mmoles) of 3-(1-adamantyl)-4-methoxybenzaldehyde and 2.6 g (14.4 mmoles) of allyl 4-aminobenzoate the synthesis is effected following the procedures described in Example 8. The resulting crude product is recrystallized in ethyl acetate. After filtration and drying, 4.1 g (76%) of the allylic ester whose melting point is 160°–162° C. are obtained.

(b) 4-[3-(1-adamantyl)-4-methoxybenylideneamino] benzoic acid

In a manner analogous to Example 1(d) starting with 2 g (4.7 mmoles) of the allylic ester prepared above in (a), 1.4 g (77%) of 4-[3-(1-adamantyl)-4-methoxybenylideneamino] benzoic acid whose melting point is 299°–301° C. are obtained.

EXAMPLE 10

4-(α-amino-3-tert.butyl-4-methoxybenzylideneamino)benzoic acid (a) allyl 4-(3-tert.butyl-4-methoxybenzamido) benzoate In a round bottom flask, there are introduced 5.92 g (33.4 mmoles) of allyl 4-aminobenzoate, 5.6 ml (40.25 mmoles) of triethylamine and 100 ml of THF. A solution of 8 g (38.4 mmoles) of 3-tert.butyl-4-methoxybenzoyl chloride dissolved in 50 ml of THF are slowly added and the mixture is stirred at ambient temperature for 4 hours. The reaction medium is poured into water and extracted with dichloromethane. The organic phase is decanted, washed with demineralized water up to pH 6, dried on $Na_2SO_4$ and filtered. The solvents are evaporated under reduced pressure. The resulting maroon oil is crystallized in hexane. The solid is filtered and recrystallized in absolute ethanol. After filtration on fritted glass and drying for 48 hours at 80° C. 5.1 g (42.5%) of the expected ester are obtained in the form of white crystals whose melting point is 180°–182° C.

(b) allyl 4-(α-chloro-3-tert.butyl-4-methoxybenzylideneamino)benzoate

Starting with 2 g (5.44 mmoles) of the derivative obtained above in (a), the synthesis is carried out following the procedures of Example 1(b). After evaporation to dryness, 2.3 g (100%) of the expected crude product are recovered which is employed as such in the following synthesis.

(c) allyl 4-(α-amino-3-tert.butyl-4-methoxybenzylideneamino benzoate

In a manner analogous to Example 1(c), by reacting 2.3 g (5.44 mmoles) of the compound obtained above in (b) with 40 ml of ammonia (33%), then extracting with ethyl acetate, and chromatographing on a silica column by eluting with a 50/50 mixture of ethyl acetate and hexane, 1.06 g (53%) of the expected product whose melting point is 120°–122° C. are obtained.

(d) 4-(α-amino-3-tert.butyl-4-methoxybenzylideneamino)benzoic acid

In a round bottom flask, there are introduced 300 mg (0.82 mmole) of the derivative obtained above in (c), 180 mg (4.5 mmoles) of soda and 10 ml of methanol. After 24 hours of reaction at reflux of the methanol, the mixture is evaporated and the remainder is taken up in water. The reaction mixture is neutralized to pH 5–6 by acetic acid. The resulting precipitate is filtered, washed with demineralized water and then dried for 48 hours at 80° C. 210 mg (78%) of the expected acid whose melting point is 170°–172° C. are obtained

EXAMPLE 11

Methyl-4-(α-chloro-5,6,7,8-tetrahydro-5,5,8,8-tetramethyl-2-naphthylmethylideneamino)benzoate (a) Methyl-4-(α-chloro-5,6,7,8-tetrahydro-5,5,8,8-tetramethyl-2-naphthylmethylideneamino)benzoate Starting with 4.94 g (13.5 mmoles) of methyl 4-(5,6,7,8-tetrahydro-5,5,8,8-tetramethyl-2-naphthyl carboxamido) benzoate, the synthesis is carried out following the procedure of Example 1(b). After evaporation to dryness, 5.7 g (100%) of the expected crude product are obtained which is used as such for the following synthesis.

(b) Methyl-4-(α-amino-5,6,7,8-tetrahydro-5,5,8,8-tetramethyl-2-naphthylmethylideneamino)benzoate In a manner analogous to Example 1(c) by reacting 5.7 g (13.5 mmoles) of the compound obtained above in (a) with 125 ml of ammonia (33%) an oily crude product is recovered which is chromatographed on a silica column in a 30/70 ethylacetate-hexane system. 600 mg (12%) of the expected ester whose melting point is 196°–198° C. are recovered.

EXAMPLE 12

4-(α-amino-5,6,7,8-tetrahydro-5,5,8,8-tetramethyl-2-naphthylmethylideneamino)benzyl alcohol In a round bottom flask, there are introduced 420 mg (1.15 mmole) of the ester obtained in Example 11 (b) and 25 ml of THF. There are then introduced, by portions, 110 mg (2.88 mmoles) of the double lithium and aluminum hydride. The mixture is stirred for 8 hours at ambient temperature. The reaction medium is hydrolyzed with hydrated sodium sulfate. The resulting precipitate is filtered and the filtrate is evaporated. 350 mg (93%) of the expected alcohol whose melting point is 171°–172° C. are obtained.

EXAMPLE 13

4-(α-amino-5,6,7,8-tetrahydro-5,5,8,8-tetramethyl-2-naphthylmethylideneamino) toluene (a) 4-(α-chloro-5,6,7,8-tetrahydro-5,5,8,8-tetramethyl-2-naphthylmethylideneamino)toluene Starting with 2 g (6.22 moles) of 4-(5,6,7,8-tetrahydro-5,5,8,8-tetramethyl-2-naphthylcarboxamido)toluene, the synthesis is carried out by following the procedures of Example 1(b). After evaporation to dryness, 2.34 g (100%) of the expected crude product are obtained which is used as such in the following synthesis.

(b) 4-(α-amino-5,6,7,8-tetrahydro-5,5,8,8-tetramethyl-2-naphthylmethylideneamino)toluene In a manner analogous to Example 1(c) by reacting 2.34 g (6.22 mmoles) of the compound obtained above in (a) with 60 ml of ammonia (33%), then extraction with ethyl acetate and chromatography on a silica column using a 40/60 ethyl acetate-hexane eluant system. 740 mg (37%) of the expected product whose melting point is 147°–149° C. are obtained.

EXAMPLE 14

4-(α-amino-5,6,7,8-tetrahydro-5,5,8,8-tetramethyl-2-naphthylmethylideneamino)benzamide (a) 4-(α-chloro-5,6,7,8-tetrahydro-5,5,8,8-tetramethyl-2-naphthylmethyl)benzoyl chloride In a round bottom flask, there are introduced 1 g (2.84 mmoles) of 4-(5,6,7,8-tetrahydro-5,5,8,8-tetramethyl-2- naphthylcarboxamidino)benzoic acid and 10 ml of thionyl chloride. The mixture is heated at reflux for 24 hours and evaporated to dryness. 1.2 g of the expected crude product (100%) are recovered which is used as such in the following synthesis.

(b) 4-(α-amino-5,6,7,8-tetrahydro-5,5,8,8-tetramethyl-2-naphthylmethylideneamino)benzamide In a round bottom flask, there are introduced 1.2 g (2.84 mmoles) of the derivative obtained in (a) above and 15 ml of THF. The mixture is stirred while maintaining the reaction medium at 0° C. 40 ml of ammonia (33%) are slowly added and the mixture is stirred for 4 hours and then extracted with ethyl acetate. The organic phase is washed until neutralized, dried on sodium sulfate and filtered. The solvents are evaporated under reduced pressure. 1 g of the crude product is recovered which is taken up in hot ethyl acetate. After filtration, 470 mg (47%) of the expected amide whose melting point is 247°–249° C. are obtained.

EXAMPLE 15

2-hydroxy-4-(α-amino-5,6,7,8-tetrahydro-5,5,8,8-tetramethyl-2-naphthylmethylideneamino)benzoic acid (a) allyl 2-hydroxy-4-aminobenzoate In a round bottom flask, there are introduced 50 ml of allyl alcohol and 460 mg (0.02 mole) of sodium while cooling with an ice bath. There is then added a solution of 8.3 g (0.05 mole) of methyl 2-hydroxy-4-amino benzoate in 100 ml of allyl alcohol. The mixture is heated while distilling the methanol formed. The mixture is evaporated to dryness, and the residue is taken up in water, acidified with 1N hydrochloric acid and, extracted with ethyl ether. The organic phase is decanted, dried on magnesium sulfate and evaporated. The residue is taken up in hexane, filtered and dried. 8.6 g (90%) of the allyl ester whose melting point is 58°–59° C. are recovered.

(b) allyl 2-hydroxy-4-(5,6,7,8-tetrahydro-5,5,8,8-tetramethyl-2-naphthylcarboxamido)benzoate In a manner analogous to Example 1(a) by reacting 6.7 g (34.7 mmole) of allyl 2-hydroxy-4-aminobenzoate with 8.7 g (34.7 mmoles) of 5,6,7,8-tetrahydro-5,5,8,8-tetramethyl-2-naphthoyl chloride, 12.7 g (90%) of the expected allyl ester which melts at 129°–130° C. are obtained.

(c) allyl 2-hydroxy-4-[α-chloro-(5,6,7,8-tetrahydro-5,5,8,8-tetramethyl-2-naphthyl)methylideneamino] benzoate In a round bottom flask, there are introduced 4 g (0.01 mole) of the preceding product and 50 ml of thionyl chloride. The mixture is heated at reflux for 24 hours. The reaction medium is evaporated to dryness and 4.2 g (100%) of the expected crude product is recovered which is used as such for the following synthesis.

(d) allyl 2-hydroxy-4-(α-amino-5,6,7,8-tetrahydro-5,5,8,8-tetramethyl-2-naphthylmethylideneamino) benzoate In a manner analogous to Example 1(c), by reacting 4.2 g (10 mmoles) of the compound obtained above in (c) with 50 ml of ammonia (33%), 2.1 g (52%) of the expected allyl ester are obtained in the form of a yellow oil.

(e) 2-hydroxy-4-(α-amino-5,6,7,8-tetrahydro-5,5,8,8-tetramethyl-2-naphthylmethylideneamino)benzoic acid In a manner analogous to Example 1(d) starting with 2.1 g (5.2 mmoles) of allyl 2-hydroxy-4-(α-amino-5,6,7,8-tetrahydro-5,5,8,8-tetramethyl-2-naphthylmethylideneamino)benzoate, 1.1 g (58%) of the expected acid whose melting point is 209°–210° C. are obtained.

EXAMPLE 16

(a) allyl 4-(α-chloro-5,6,7,8-tetrahydro-5,5,8,8-tetramethyl-2-naphthylmethylideneamino)benzoate In a round bottom flask, there are introduced 40.5 (0.103 mole) of allyl 4-(5,6,7,8-tetrahydro-5,5,8,8-tetramethyl-2-naphthylcarboxamido)benzoate and 500 ml of thionylchloride. The mixture is heated at reflux for 48 hours. The reaction mixture is evaporated to dryness. The residue is crystallized in hexane, filtered, washed with hexane and dried under a vacuum. 16.86 g (47%) of the expected product whose melting point is 80° C. are recovered.

(b) allyl 4-(α-anilino-5,6,7,8-tetrahydro-5,5,8,8-tetramethyl-2-naphthylmethylideneamino)benzoate In a round bottom flask, there are introduced 4.08 ml (44.8 mmoles) of aniline and 10 ml of THF. 4 g (8.97 mmoles) of the compound obtained in (a) above, dissolved in 40 ml of THF are slowly added. The mixture is stirred at ambient temperature for 24 hours. The reaction medium is poured into water, acidified to pH 5 with 1N hydrochloric acid, extracted with ethyl acetate and washed with water. The organic phase is decanted, dried on sodium sulfate and evaporated. The resulting residue is purified by chromatography on a silica column eluted with an 85/15 mixture of hexane and ethyl acetate. After evaporation of the solvents, 3.6 g (87%) of a yellow oil are obtained.

(c) 4-(α-anilino-5,6,7,8-tetrahydro-5,5,8,8-tetramethyl-2-naphthylmethylideneamino)benzoic acid In a round bottom flask, there are introduced 3.55 g (7.62 mmoles) of the allyl ester obtained in Example 16(a) and 70 ml of THF. 880 mg (0.76 mmole) of tetrakis (triphenylphosphine)palladium (O) are added and then 6.64 ml (76.2 mmoles) of morpholine are slowly added. The mixture is stirred at ambient temperature for 1 hour. The reaction medium is poured into water, acidified to pH 5 with acetic acid, extracted with ethyl acetate, washed with water, dried on sodium sulfate and evaporated. The resulting residue is purified by chromatography on a silica column eluted with a 50/50 mixture of ethyl acetate and hexane. After evaporation of the solvents 3.05 g (95%) of the expected acid whose melting point is 125°–130° C. are obtained.

EXAMPLE 17

The hydrochloride of 4-(α-anilino-5,6,7,8-tetrahydro-5,5,8,8-tetramethyl-2-naphthylmethylideneamino)benzoic acid In a round bottom flask, there are introduced 500 mg (1.17 mmole) of the acid obtained in Example 16(c) and 15 ml of acetone. 1.12 ml of hydrochloric acid (1.045N) are added. The precipitate is filtered, washed with acetone and dried. 490 mg (90%) of the expected hydrochloride whose melting point is 297° C. (with decomposition) are recovered.

EXAMPLE 18

4-(α-benzylamino-5,6,7,8-tetrahydro-5,5,8,8-tetramethyl-2-naphthylmethylideneamino)benzoic acid (a) allyl 4-(α-benzylamino-5,6,7,8-tetrahydro-5,5,8,8-tetramethyl-2-naphthylmethylideneamino)benzoate In a manner analogous to Example 16(b) starting with 5 g (11.2 mmoles) of the compound obtained in Example 16(a) and 5.67 ml (52 mmoles) of benzylamine, 3.5 g (67.3%) of the expected allyl ester are obtained in the form of a yellow oil.

(b) 4-(α-benzylamino-5,6,7,8-tetrahydro-5,5,8,8-tetramethyl-2-naphthylmethylideneamino)benzoic acid In a manner analogous to Example 16(c) starting with 3.5 g (7.3 mmoles) of the allyl ester obtained in Example 18(a) there are obtained, after chromatography on a silica column eluted with a 60/40 mixture of ethyl acetate and hexane, and evaporation of the solvents, 2.45 g (76.6.%) of the expected acid whose melting point is 105° C.

EXAMPLE 19

4-(α-dimethylamino-5,6,7,8-tetrahydro-5,5,8,8-tetramethyl-2-naphthylmethylideneamino)benzoic acid (a) allyl 4-(α-dimethylamino-5,6,7,8-tetrahydro-5,5,8,8-tetramethyl-2-naphthylmethylideneamino)benzoate In a manner analogous to Example 16(b) starting with 4 g (8.97 mmoles) of the compound obtained in Example 16(a) and 5.63 ml (0.452 mole) of dimethylamine (40% in water) 3.33 g (89%) of the expected allyl ester are obtained in the form of a yellow oil.

(b) 4-(α-dimethylamino-5,6,6,7-tetrahydro-5,5,8,8-tetramethyl-2-naphthylmethylideneamino)benzoic acid In a manner analogous to Example 16(c) starting with 3.3 g (7.92 mmoles) of the allyl ester obtained in Example 19(a) 2.5 g (83%) of the expected acid whose melting point is 240° C. are obtained.

EXAMPLE 20

4-[$N^2$-(5,6,7,8-tetrahydro-5,5,8,8-tetramethyl-2-naphthyl)amidino]benzoic acid (a) methyl 4-[$N^2$-(5,6,7,8-tetrahydro-5,5,8,8-tetramethyl-2-naphthyl)amidino]benzoate In a manner analogous to Example 11(b) by reacting 2.5 g (6.9 mmoles) of methyl 4-(5,6,7,8-tetrahydro-5,5,8,8-tetramethyl-2-naphthylcarbamoyl)benzoate with 25 ml of thionyl chloride, there is recovered, after evaporation, the corresponding chloride compound which is directly reacted with 100 ml of ammonia (33%). After recrystallization in a mixture of ethyl acetate and hexane, 1.5 g (59.8%) of the expected ester whose melting point is 218°–220° C. are obtained.

(b) 4-[$N^2$-(5,6,7,8-tetrahydro-5,5,8,8-tetramethyl-2-naphthyl)amidino]benzoic acid In a manner analogous to Example-10(d) starting with 500 mg (1.37 mmole) of the ester obtained previously in (a), 300 mg (62%) of the expected acid whose melting point is 281°–284° C. are obtained.

EXAMPLE 21

4-[$N^1$-phenyl-$N^2$-(5,6,7,8-tetrahydro-5,5,8,8-tetramethyl-2-naphthyl)amidino]benzoic acid (a) methyl 4-[$N^1$-phenyl-$N^2$-(5,6,7,8-tetrahydro-5,5,8,8-tetramethyl-2-naphthyl)amidino]benzoate In a manner analogous to Example 20(a), the synthesis is carried out starting with 2.9 g (6.9 mmoles) of the chloride compound prepared in Example 20(a) and 3.2 ml (34.5 mmoles) of aniline. After chromatography on a silica column using a 20/80 mixture of ethylacetate and hexane and washing with hot hexane, 390 mg (13%) of the expected ester whose melting point is 163°–164° C. are isolated.

(b) 4-[$N^1$-phenyl-$N^2$-(5,6,7,8-tetrahydro-5,5,8,8-tetramethyl-2-naphthyl)amidino]benzoic acid In a manner analogous to Example 10(d) starting with 300 mg (0.68 mmole) of the derivative obtained above in (a), 230 mg (79%) of the expected acid whose melting point is 281°–284° C. are isolated.

EXAMPLE 22

The hydrochloride of 4-(α-amino-5,6,7,8-tetrahydro-5,5,8,8-tetramethyl-2-naphthylmethylideneamino)phenol (a) 4-(α-chloro-5,6,7,8-tetrahydro-5,5,8,8-tetramethyl-2-naphthylmethylideneamino)anisole In a manner analogous to Example 1(b) by reacting 3 g (8.9 mmoles) of 4-(5,6,7,8-tetrahydro-5,5,8,8-tetramethyl-2-naphthylcarboxamido)anisole with 30 ml of thionyl chloride, the expected chloride compound is recovered and used as such in the following synthesis.

(b) 4-(α-amino-5,6,7,8-tetrahydro-5,5,8,8-tetramethyl-2-naphthylmethylideneamino)anisole In a manner analogous to Example 1(c) by reacting 8.9 mmoles of the compound obtained above in (a) with 62 ml of ammonia (33%) and after recrystallization in hexane, 1.22 g (40%) of the expected product whose melting point is 138°–140° C. are isolated.

(c) The hydrochloride of 4-(α-amino-5,6,7,8-tetrahydro-5,5,8,8-tetramethyl-2-naphthylmethylideneamino)phenol In a round bottom flask, there are introduced 800 mg (2.38 mmoles) of the derivative previously obtained in (b) and 5 g (43.3 mmoles) of pyridine hydrochloride. The reaction mixture is progressively heated to 190°–200° C. with vigorous stirring and this temperature is maintained for 1 hour. The reaction mixture is returned to 100° C. and a large excess of water is added. The resulting precipitate is filtered, washed abundantly with demineralized water and dried for 48 hours at 80° C. 500 mg (59%) of the expected phenol whose melting point is 255°–256° C. are obtained.

EXAMPLE 23

4-(α-methylimino-N-methyl-5,6,7,8-tetrahydro-5,5,8,8-tetramethyl-2-naphthylmethylamino)benzoic acid (a) N-methyl-(5,6,7,8-tetrahydro-5,5,8,8-tetramethyl-2-naphthyl)amide In a round bottom flask, there are introduced 0.75 g (43 mmoles) of 5,6,7,8-tetrahydro-5,5,8,8-tetramethyl-2- naphthoyl chloride and 70 ml of THF. 10 ml of N-methylamine (40% in water) are slowly added and the mixture is stirred for 8 hours at ambient temperature. The reaction mixture is poured into water. The resulting precipitate is filtered, washed until neutral and dried for 24 hours at 80° C. 10.16 g (96.5%) of the expected amide whose melting point is 136°–140° C. are obtained.

(b) methyl 4-(α-methylimino-N-methyl-5,6,7,8-tetrahydro-5,5,8,8-tetramethyl-2-naphthylmethylamino)benzoate In a manner analogous to Example 11(b) by reacting 1.5 g (6.12 mmoles) of the derivative previously obtained in (a) with 20 ml of thionyl chloride, there is recovered, after evaporation, the corresponding chloride compound that is diluted in 25 ml of THF. There are then added, at ambient temperature, 2 g (12.12 mmoles) of methyl 4-(N-methylamino)benzoate dissolved in 20 ml of THF and the mixture is stirred for 8 hours. After chromatography on a silica column eluted with ethyl acetate 380 mg (16%) of the expected ester whose melting point is 225°–230° C. are isolated.

(c) 4-(α-methylimino-N-methyl-5,6,7,8-tetrahydro-5,5,8,8-tetramethyl-2-naphthylmethylamino)benzoic acid In a round bottom flask, there are introduced 250 mg (0.64 mmole) of the ester previously obtained in (b), 630 mg (15.8 mmoles) of soda and 12 ml of methanol. The reaction medium is maintained at reflux for 4 hours and the methanol is then evaporated. The residue is taken up in water, neutralized with acetic acid and evaporated to dryness. The residue is taken up in THF and filtered. The filtrate is evaporated and an oil which precipitates in hexane is obtained. After filtration, 35 mg (14.5%) of the expected acid whose melting point is 275°–280° C. are isolated.

Examples of Compositions

A. Oral Compositions (a) 0.2 g tablet

| Compound of Example 1 | 0.001 g |
|---|---|
| Starch | 0.114 g |
| Dicalciumphosphate | 0.020 g |
| Silica | 0.020 g |
| Lactose | 0.030 g |
| Talc | 0.010 g |
| Magnesium stearate | 0.005 g |

In this example, the compound of Example 1 can be replaced by the same amount of the compound of Example 2.

(b) Drinkable suspension in 5 ml ampoules

| Compound of Example 3 | 0.500 g |
|---|---|
| Glycerine | 0.500 g |
| Sorbitol, 70% | 0.500 g |
| Sodium saccharinate | 0.010 g |
| Methyl parahydroxybenzoate | 0.040 g |
| Flavor, sufficient amount | |
| Purified water, sufficient amount for | 5 ml |

In this example, the compound of Example 3 can be replaced by the same amount of the compound of Example 4.

(c) 0.8 g tablet

| Compound of Example 7 | 0.500 g |
|---|---|
| Pregelatinized starch | 0.100 g |
| Microcrystalline cellulose | 0.115 g |
| Lactose | 0.075 g |
| Magnesium stearate | 0.010 g |

In this example the compound of Example 7 can be replaced by the same amount of the compound of Example 9.

(d) Drinkable suspension in 10 ml ampoules

| Compound of Example 5 | 0.200 g |
|---|---|
| Glycerine | 1.000 g |
| Sorbitol, 70% | 1.000 g |
| Sodium saccharinate | 0.010 g |
| Methyl parahydroxybenzoate | 0.080 g |
| Flavor, sufficient amount | |
| Purified water, sufficient amount for | 10 ml |

B. Topical Compositions (a) Ointment

| Compound of Example 1 | 0.020 g |
|---|---|
| Isopropyl myristate | 81.700 g |
| Fluid petrolatum oil | 9.100 g |
| Silica, sold under the trade name "AEROSIL 200" by Degussa | 9.180 g |

In this example, the compound of Example 1 can be replaced by the same amount of the compound of Example 2.

(b) Ointment

| Compound of Example 3 | 0.300 g |
|---|---|
| White petrolatum codex, sufficient amount for | 100 g |

In this example, the compound of Example 3 can be replaced by the same amount of the compound of Example 4.

(c) Nonionic water-in-oil cream

| Compound of Example 7 | 0.100 g |
|---|---|
| Mixture of emulsive lanolin alcohols, waxes and raffinated oils, sold under the trade name "EUCERINE ANHYDRE" by BDF | 39.900 g |
| Methyl parahydroxybenzoate | 0.075 g |
| Propyl parahydroxybenzoate | 0.075 g |
| Sterile, demineralized water, sufficient amount for | 100 g |

In this example the compound of Example 7 can be replaced by the same amount of the compound of Example 9.

(d) Lotion

| Compound of Example 5 | 0.100 g |
|---|---|
| Polyethylene glycol (PEG 400) | 69.900 g |
| Ethanol, 95% | 30.000 g |

(e) Hydrophobic ointment

| Compound of Example 6 | 0.300 g |
|---|---|
| Isopropyl myristate | 36.400 g |
| Silicone oil, sold under the trade name "RHODORSIL 47 V 300" by Rhone Poulenc | 36.400 g |
| Beeswax | 13.600 g |
| Silicone oil, sold under the trade name "ABIL 300.000 cst" by Goldschmidt, in an amount sufficient for | 100 g |

(f) Nonionic oil-in-water cream

| Compound of Example 8 | 1.000 g |
|---|---|
| Cetyl alcohol | 4.000 g |
| Glycerol monostearate | 2.500 g |
| Stearate of "PEG 50" | 2.500 g |
| Karite butter | 9.200 g |
| Propylene glycol | 2.000 g |
| Methyl parahydroxybenzoate | 0.075 g |
| Propyl parahydroxybenzoate | 0.075 g |
| Sterile, demineralized water, sufficient amount for | 100 g |

We claim:

1. A process for the treatment of dermatalogic, rheumatismal, respiratory or ophtalmologic ailments comprising administering to a human or animal host, a therapeutically effective amount of a pharmaceutical composition comprising in a pharmaceutically acceptable vehicle, for enteral, parenteral, topical or ocular administration to a human or an animal, a therapeutically effective amount of at least one bi-aromatic compound having the formula

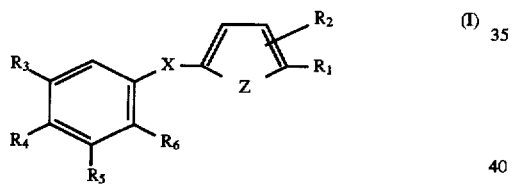

wherein $R_1$ represents hydrogen, —OH, —$CH_3$, —$CH_2OH$, —$COR_7$, —$CH(OH)CH_3$, —$CH_2OCOR_8$, —$SO_2R_9$, —$SOR_9$ or —$SR_9$ $R_7$ represents hydrogen, —OH, —$OR_{10}$,

lower alkyl, monohydroxyalkyl, or polyhydroxyalkyl, $R_8$ represents linear or branched alkyl having 1–20 carbon atoms, or alkenyl having 2–20 carbon atoms, $R_9$ represents —OH, lower alkyl or

$R_{10}$ represents alkyl having 1–20 carbon atoms or alkenyl having 2–20 carbon atoms, r' and r'', each independently, represent hydrogen; lower alkyl; phenyl; phenyl substituted by at least one of a halogen, hydroxyl or nitro function; aralkyl; a heterocycle selected from the group consisting of piperidino, morpholino, pyrrolidino or piperazino, optionally substituted in the 4 position by a $C_1$–$C_6$ alkyl or mono or polyhydroxyalkyl; or r' and r'' taken together form said heterocycle;

$R_2$ and $R_6$ represent hydrogen, OH, lower alkyl, alkoxy having 1–6 carbon atoms, fluorine, chlorine or $CF_3$.

$R_3$ represents α,α'-disubstituted alkyl having 4–12 carbon atoms or mono or polycyclic cycloalkyl having 5–12 carbon atoms whose linking carbon is trisubstituted, $R_5$ is hydrogen, or $R_4$ represents hydrogen, OH, alkoxy having 1–6 carbon atoms, α,α'-disubstituted alkyl having 4–12 carbon atoms or $R_3$ and $R_4$ or $R_4$ and $R_5$ taken together form, with the adjacent benzene ring, a ring having 5 or 6 carbon atoms substituted by 2 to 6 methyl groups, Z represents an oxygen or sulfur atom, —CH=$CR_{11}$— or —N=$CR_{12}$—, $R_{11}$ represents hydrogen, OH or lower alkyl, $R_{12}$ represents hydrogen or lower alkyl, X is selected from the group consisting of

 (iii)

and

 (iv)

$R_{13}$ represents $R_{16}$, $OR_{16}$, —$SR_{16}$ or

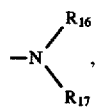

$R_{16}$ and $R_{17}$ represent hydrogen, lower alkyl, fluoro lower alkyl, alkenyl having 2–6 carbon atoms, alkynyl having 2–6 carbon atoms, phenyl, phenyl substituted by at least one of halogen, hydroxyl or nitro functions, or aralkyl, $R_{14}$ represents lower alkyl, $R_{15}$ represents lower alkyl or fluoro lower alkyl, and the salts of said compound of Formula (I) obtained by the addition of a base when $R_1$ represents a carboxylic acid function or by the addition of an acid.

2. The process of claim 1 wherein said compound is in the form of a salt of an alkali metal, an alkaline earth metal, zinc or an organic amine.

3. The process of claim 1 wherein said compound is in the form of a salt of a mineral or organic acid selected from the group consisting of hydrochloric acid, sulfuric acid, acetic acid, citric acid, fumaric acid, hemisuccinic acid, maleic acid and mandelic acid.

4. The process of claim 1 wherein each of said lower alkyl groups is selected from the group consisting of methyl, ethyl, isopropyl, butyl and ter butyl.

5. The process of claim 1 wherein each of said alkoxy groups having 1–6 carbon atoms is selected from the group consisting of methoxy, ethoxy, isopropoxy and butoxy.

6. The process of claim 1 wherein said α,α'-disubstituted alkyl is selected from the group consisting of tert.butyl, 1,1-dimethylpropyl, 1-methyl-1-ethylpropyl, 1-methyl-1-ethylhexyl and 1,1-dimethyldecyl.

7. The process of claim 1 wherein said mono or polycyclic cycloalkyl having 5–12 carbon atoms whose linking carbon is trisubstituted is 1-methyl cyclohexyl or 1-adamantyl.

8. The process of claim 1 wherein said monohydroxyalkyl is 2-hydroxyethyl, 2-hydroxypropyl or 3-hydroxypropyl.

9. The process of claim 1 wherein said polyhydroxyalkyl has 2–6 carbon atoms and 2–5 hydroxy groups and is selected from the group consisting of 2,3-dihydroxypropyl, 2,3,4-trihydroxybutyl, 2,3,4,5-tetrahydroxypentyl and pentaerythrityl.

10. The process of claim 1 wherein said aralkyl is benzyl or phenethyl, optionally substituted by at least one of halogen, hydroxyl or a nitro function.

11. The process of claim 1 wherein said alkynyl having 2–6 carbon atoms is propargyl.

12. The process of claim 1 wherein said alkenyl having 2–6 carbon atoms is selected from the group consisting of vinyl, propenyl, 2-methyl propenyl and butene-2-yl.

13. The process of claim 1 wherein said fluoro lower alkyl has 1–6 carbon atoms and 3–7 fluoroine atoms.

14. The process of claim 1 wherein said compound is selected from the group consisting of 4-(α-methylamino-5,6,7,8-tetrahydro-5,5,8,8-tetramethyl-2-naphthylmethylideneamino)benzoic acid, 4-(α-amino-5,6,7,8-tetrahydro-5,5,8,8-tetramethyl-2-naphthylmethylideneamino)benzoic acid, 4-[5-(1-adamantyl)-2-hydroxy-4-methoxybenzylideneamino]benzoic acid, 4-[α-amino-3-(1-adamantyl)-4-methoxybenzylideneamino]benzoic acid, the hydrochloride of 4-[α-methylamino-3-(1-adamantyl)-4-methoxybenzylideneamino]benzoic acid, 4-[α-methylthio-3-(1-adamantyl)-4-methoxybenzylideneamino]benzoic acid, 4-[α-methoxy-3-(1-adamantyl)-4-methoxybenzylideneaino]benzoic acid, methyl 4-[3-(1-adamantyl)-4-methoxybenzylideneamino]benzoate, 4-[3-(1-adamantyl)-4-methoxybenzylideneamino]benzoic acid, 4-(α-amino-3-tert.butyl-4-methoxybenzylideneamino)benzoic acid, methyl 4-(α-amino-5,6,7,8-tetrahydro-5,5,8,8-tetramethyl-2-naphthylmethylideneamino)benzoate, 4-(α-amino-5,6,7,8-tetrahydro-5,5,8,8-tetramethyl-2-naphthylmethylideneamino)benzyl alcohol, 4-(α-amino-5,6,7,8-tetrahydro-5,5,8,8-tetramethyl-2-naphthylmethylideneamino)toluene, 4-(α-amino-5,6,7,8-tetrahydro-5,5,8,8-tetramethyl-2-naphthylmethylideneamnino)benzamide, 2-hydroxy-4-(α-amino-5,6,7,8-tetrahydro-5,5,8,8-tetramethyl-2-naphthylmethylideneamino)benzoic acid, allyl 4-(α-chloro-5,6,7,8-tetrahydro-5,5,8,8-tetramethyl-2-naphthylmethylideneamino)benzoate, 4-(α-anilino-5,6,7,8-tetrahydro-5,5,8,8-tetramethyl-2-naphthylmethylideneamino)benzoic acid, the hydrochloride of 4-(α-anilino-5,6,7,8-tetrahydro-5,5,8,8-tetramethyl-2-naphthylmethylideneamino)benzoic acid, 4-(α-benzylamino-5,6,7,8-tetrahydro-5,5,8,8-tetramethyl-2-naphthylmethylideneamino)benzoic acid, 4-(α-dimethylamino-5,6,7,8-tetrahydro-5,5,8,8-tetramethyl-2-naphthylmethylideneamino)benzoic acid, 4-[$N^2$-(5,6,7,8-tetrahydro-5,5,8,8-tetramethyl-2-naphthyl)amidino]benzoic acid, 4-[$N^1$-phenyl-$N^2$-(5,6,7,8-tetrahydro-5,5,8,8-tetramethyl-2-naphthyl)amidino]benzoic acid, the hydrochloride of 4-(α-amino-5,6,7,8-tetrahydro-5,5,8,8-tetramethyl-2-naphthylmethylideneamino)phenol and 4-(α-methylamino-N-methyl-5,6,7,8-tetrahydro-5,5,8,8-tetramethyl-2-naphthylmethylamino)benzoic acid.

15. The process of claim 1, wherein said compound of formula (I) is present in said composition in an amount ranging from 0.001 to about 5% by weight based on the total weight of said composition.

16. The process of claim 1, wherein said compound of formula (I) is present in said composition in an amount ranging from 0.001 to 3% by weight based on the total weight of said composition.

* * * * *